United States Patent
Dysarz

(10) Patent No.: US 6,193,690 B1
(45) Date of Patent: *Feb. 27, 2001

(54) INCLINED PLANE LATCHING DEVICE FOR AN IV CATHETER

(76) Inventor: Edward D. Dysarz, 18 Front St, Rockport, TX (US) 78382

( * ) Notice: Under 35 U.S.C. 154(b), the term of this patent shall be extended for 0 days.

This patent is subject to a terminal disclaimer.

(21) Appl. No.: 09/422,158

(22) Filed: Oct. 22, 1999

Related U.S. Application Data

(63) Continuation of application No. 09/130,969, filed on Aug. 7, 1998, now Pat. No. 5,997,507.

(51) Int. Cl.[7] .................................................. A61M 5/178
(52) U.S. Cl. ........................ 604/161; 604/263; 604/110; 604/164.12; 604/168.01
(58) Field of Search ..................... 604/110, 158, 604/168.01, 171, 181, 187, 195, 263, 198, 161, 164.01, 164.13

(56) References Cited

U.S. PATENT DOCUMENTS

| | | |
|---|---|---|
| 3,306,290 | 2/1967 | Weltman . |
| 4,392,859 | 7/1983 | Dent . |
| 4,973,316 | 11/1990 | Dysarz . |
| 4,978,343 | 12/1990 | Dysarz . |
| 5,019,144 | 5/1991 | Tsao . |
| 5,084,018 | 1/1992 | Tsao . |
| 5,120,310 | 6/1992 | Shaw . |
| 5,267,961 | 12/1993 | Shaw . |
| 5,385,551 | 1/1995 | Shaw . |
| 5,389,076 | 2/1995 | Shaw . |

*Primary Examiner*—Sharon Kennedy
*Assistant Examiner*—Deborah Blyveis

(57) ABSTRACT

A intravenous catheter device having a biased spring hard needle, disposed in a soft catheter. The biased spring hard needle is held within an elongated hollow barrel wherein the biased spring hard needle is extended past the first end of the soft catheter, and is further disposed in the inside of the soft catheter and further extends past the first end of the elongated hollow barrel wherein the biased spring hard needle is pulled into an almost straight line wherein the second end of the biased spring hard needle is fixed to an end cap at the second end of the elongated hollow barrel. The biased spring hard needle is held within the soft catheter and the elongated hollow barrel by an inclined plane latching device. When the inclined plane latching device is disengaged with the biased spring hard needle, the spring section of the biased spring hard needle that is near the second end of the biased spring hard needle instantly withdraws the first end of the biased spring hard needle out of the soft catheter and further withdraws the first end of the biased spring hard needle out of the first end of the elongated hollow barrel wherein the first end of the biased spring hard needle cannot accidentally prick or injure a person thereby preventing an accidental injection of bacteria, virus or other undesirable material into a person.

14 Claims, 4 Drawing Sheets

INCLINED PLANE LATCHING DEVICE FOR AN IV CATHETER

This application is a continuation of U.S. patent application Ser. No. 09/130,969 filed on Aug. 7, 1998 now U.S. Pat. No. 5,997,507.

BACKGROUND OF THE INVENTION

There are several types of safety intravenous catheter designs. Most of the designs are similar to syringes or blood sampling devices that are available today. One such design is shown in a patent issued to JAGGER et al on Jun. 3, 1986 U.S. Pat. No. 4,592,744. This is a safety blood sampling device however it requires two (2) hands to operate or to cover the needle cannula.

Blood samples are also taken with syringes and there are also many safety syringes available. Some of these designs have a sleeve or sheath that will cover the needle after it has been used. Some typical designs with sleeves or sheaths are Z. M. ROEHR et al U.S. Pat. No. 3,008,570, Z. M. ROEHR U.S. Pat. No. 3,107,785, BARTNER, et al U.S. Pat. No. 3,895,633, G. K. BURKE U.S. Pat. No. 3,306,291, GYURE et al U.S. Pat. No. 4,300,678, WINSTEAD HALL U.S. Pat. No. 4,356,822, SAMPSON U.S. Pat. No. 4,425,120, LARSON U.S. Pat. No. 4,639,249, HARBAUGH U.S. Pat. No. 4,655,751, STRAUSS U.S. Pat. No. 4,664,654, BRAGINETZ U.S. Pat. No. 466,435, SPENCER U.S. Pat. No. 4,702,738, MILORAD U.S. Pat. No. 4,702,739, SPENCER U.S. Pat. No. 4,801,295, PONCY U.S. Pat. No. 4,816,022, and HUGHES U.S. Pat. No. 4,840,619.

Other designs have a retractable needle such as WELTMAN U.S. Pat. No. 3,306,290, and DENT U.S. Pat. No. 4,392,859. These designs do not have a means whereby the needle is extended from the syringe and held in place in a positive and rigid position in order to first inject the needle prior to injecting the medication. Still other designs have methods of bending to render the needle harmless after the medication has been injected. Most of these designs have one major purpose and that is to prevent the spread of infectious diseases such as aids, hepatitis, or other diseases from an accidental injection with a contaminated needle into others after the needle of the syringe was inserted into a patient with the above mentioned disease. These various designs all work well to a degree, but they all fall short of their intended purpose during the act of covering the needle, or removing the needle, which requires two hands.

Other devices such as TSAO U.S. Pat. No. 5,019,044, TSAO U.S. Pat. No. 5,084,018, SHAW U.S. Pat. No. 5,267,961, SHAW U.S. Pat. No. 5,120,310, DYSARZ U.S. Pat. No. 4,978,343 and DYSARZ U.S. Pat. No. 4,973,316 are all capable of releasing the needle if the container that they are packed in are dropped or jarred severly.

These devices do not have a protective latching means but they rely on friction to restrain the needle with a biased spring.

SUMMARY

It is the object of this invention to provide an intravenous catheter device with a fail safe latch and release means wherein the latch and release means will not cause the needle to retract in the event of a shock due to dropping the packaged IV catheter.

Another object of the present invention is to render the needle of the intravenous catheter device useless after the needle is retracted into the flashback chamber of the intravenous catheter device to prevent the accidental reuse of the contaminated needle or to further prevent the reuse and abuse by users of illicit drugs.

It is still another object of the present invention to further prevent the accidental release of the needle cannula after the needle is in the flashback chamber of the intravenous catheter device.

The foregoing and other objects and advantages are attained by a device, an elongated hollow barrel, a spring needle, hub post and an end cap in combination with a failsafe latch and release means wherein when said intravenous catheter is used to inject a soft needle cannula into a vein in the body or part of the body in order to inject medication or other fluid at a consistent rate into the body, the fail safe latch and release means releases the biased spring needle cannula and further pulls the spring needle cannula into the flash back chamber of the intravenous catheter device rendering the contaminated spring needle cannula harmless to prevent the accidental pricking of others and to prevent a contaminated spring needle cannula from being released from the flash back chamber of the intravenous catheter device.

The features of the present invention can be best understood together with further objects and advantages by reference to the following descriptions taken in connection with accompanying drawings, wherein like numerals indicate like parts.

BRIEF DESCRIPTION OF THE DRAWINGS

FIG. 5 is a section elevation view of the device showing the needle release button being pressed in.

DETAILED DESCRIPTION OF THE PREFERRED EMBODIMENT

Figure 1:
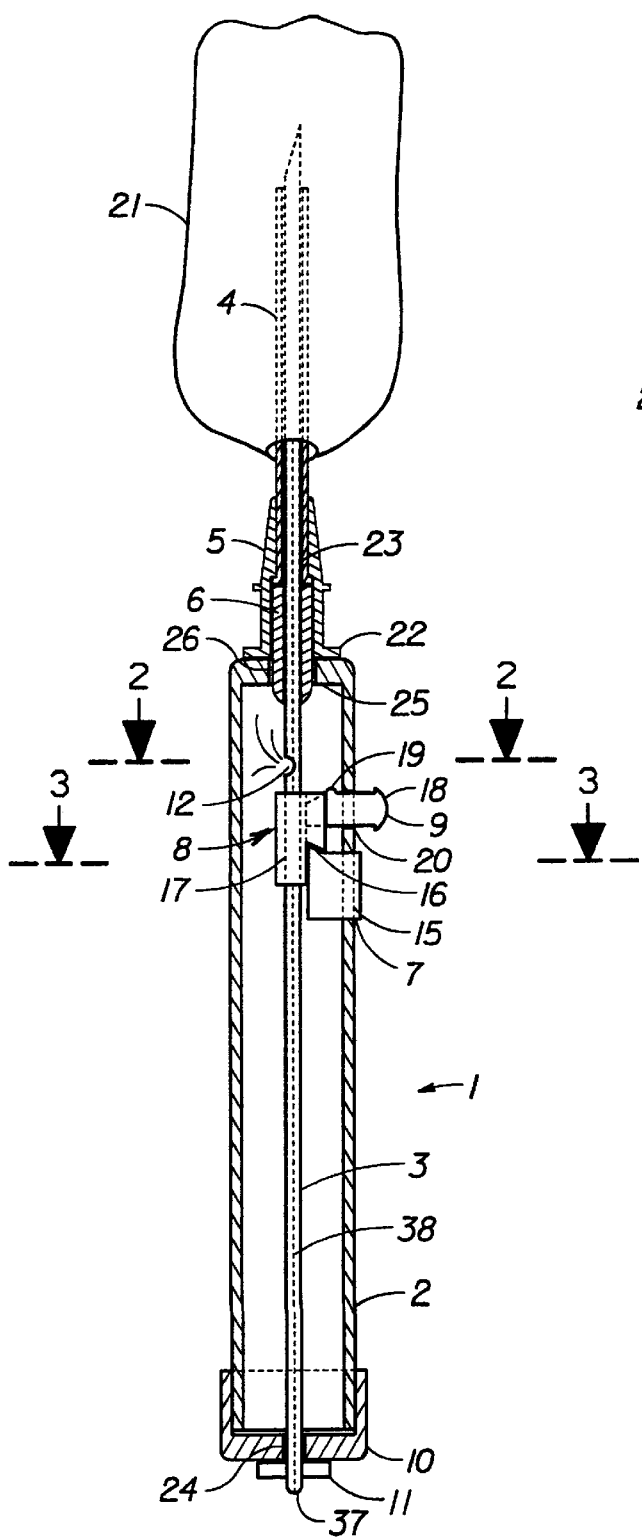
FIG. 1 is a section elevation view of the device of the preferred embodiment of the present invention.

Referring to FIG. 1 there is shown a section elevation view of the device 1 of the preferred embodiment.

The intravenous catheter device 1 is comprised of a flash back chamber 2 that has a first end, a second end and is circumferential in section with an inside surface and an outside surface. A latch foundation 7 is shown suitably fixed to the flash back chamber 2 that is formed into an elongated hollow cylinder with an inside surface and an outside surface, wherein the latch foundation 7 is inserted into the first hole 15 formed in the flash back chamber 2 near the first end of the flash back chamber 2. The first hole 15 extends from the outside surface to the inside surface of the flash back chamber 2. The latch foundation 7 is inserted into the first hole 15 wherein the latch foundation 7 is suitably fixed to the first hole 15 by adhesive welding or other suitable means. The latch foundation will be described in greater detail in FIG. 3 and FIG. 4.

The inclined plane latch 8 is shown with a first end, a second end, a third end, a fourth end and a latch inclined plane 30 formed on said third end. A needle hole 17 is formed in the inclined plane latch 8 wherein the needle hole extend from the first end to the second end of the inclined plane latch 8. The biased spring hard needle 3 is suitably disposed in the needle hole 17 wherein the biased spring hard needle 3 is suitably fixed to the inclined plane latch 8 by adhesive, welding or some other suitable means. The inclined plane latch 8 is shown suitably attached to the latch foundation 7.

The inclined plane latching device 8 is shown with the needle release button 9 that has a first end and a second end. A depressor knob 18 is shown at the first end wherein a finger or thumb will most likely press the depressor knob 18 to disengage the inclined plane latch 8 from the latch foundation 7. The stop knob 19 is shown at the second end of the needle release button 9. The stop knob 19 prevents the needle release button 9 from falling out of the needle release hole 20. The needle release hole 20 is shown near the first end of the flash back chamber 2 and extends from the inside surface to the outside surface of the flash back chamber 2.

The soft catheter 4 is shown with a first end and a second end. The first end of the soft catheter 4 is shown inserted into a body 21 and the second end of the soft catheter 4 is shown suitably fixed to the first end of the first hub 5. The second end of the first hub 5 is a hollow tube and is disposed about the first end of the hub post 6. The first hub 5 is held in place and is supported on the hub post 6 by friction which will allow the hub post 6 to pull out of the first hub 5 with little force. The first hub 5 has a hub flange 22 at the second end of the first hub 5 to allow the first hub 5 to be fastened to an intravenous tube that is not shown and is not the subject of this invention. As stated, the first end of the hub post 6 is disposed in the inside surface of the second end of the first hub 5 and held in place by friction or some other suitable means. A hub post hole 23 is formed in the hub post 6 wherein the hub post hole 23 extends from the first end of the hub post 6 to the second end of the hub post 6. The biased spring hard needle 3 is disposed in the hub post hole 23 and suitably fixed to the hub post 6 along the portion of the hub post hole 23 that is disposed in the hub post 6 by adhesive, welding or friction or some other suitable means by design choice.

A flash back chamber flange 25 is shown at the first end of the flash back chamber 2 and a flange hole 26 is shown formed on the flash back chamber flange 25 that extends from the first side to the second side of the flash back chamber flange 25.

The biased spring hard needle 3 is essentially comprised of a first section from the point at the first end, to the second end of the inclined plane latch 8. The second section of the biased spring hard needle essentially extends from the second end of the inclined plane latch 8 to the loop 37. The second section of the biased spring hard needle is mostly comprised of the biased spring. The first section has a first end and a second end, and the second section has a first end and a second end.

The first section of the biased spring hard needle 3 is shown extending past the first end of the soft catheter 4 wherein the first section of the biased spring hard needle 3 is loosely disposed in the soft catheter 4. The second end of the first section of the biased spring hard needle 3 is further disposed in and suitably fixed to the hub post 6 and the inclined plane latch 8 at the second end of the first section wherein the second section of the biased spring hard needle 3 extends to the second end of the flash back chamber 2 and is shown extending through a cap hole 24 formed in the end cap 10 wherein the second end of the second section of the biased spring hard needle 3 is hooked around an end bar 11. The second end of the second section of the biased spring hard needle 3 is hooked around the end bar 11 to allow a bias or tension to exist between the latch foundation 7 and the end bar 11. Although the end bar 11 is shown as a suitable means for holding the second end of the biased spring hard needle 3 other means such as adhesive, welding or other suitable means could be used to hold the second end of the biased spring hard needle 3 to the end cap 10 or the second end of the flash back chamber 2.

A fluid release hole 12 is shown formed in the side of the biased spring hard needle 3 to allow blood or other fluid to flow out of the cannula 38 formed on the inside of the biased spring hard needle 3. If the biased spring hard needle 3 is required to be hollow the blood flow out of the fluid release hole 12 will inform a person inserting the biased spring hard needle 3 into a body if the biased spring hard needle 3 is in a vein, artery or whatever it may be inserted into. The fluid release hole 12 may or may not be necessary to the operation of the device 1.

The biased spring hard needle 3 acts as a transverse spring and maintains pressure on the needle release button 9 through the inclined plane latch 8 to keep the needle release button 9 projecting out of the flash back chamber 2.

Figure 2:
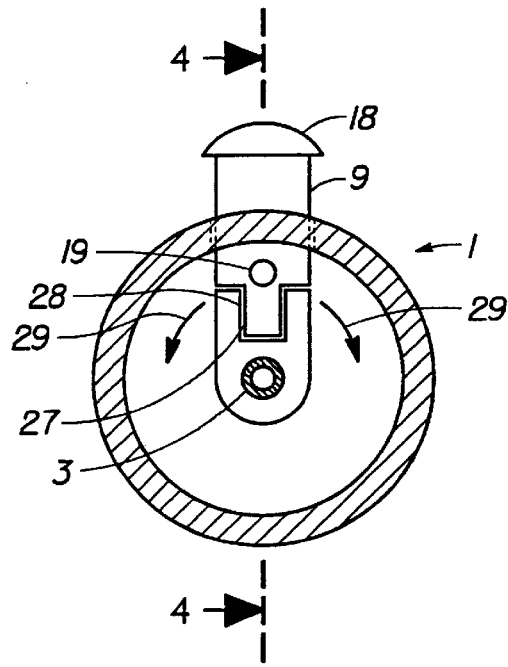
FIG. 2 is a section elevation view of the device as taken through FIG. 1.

Referring to FIG. 2 there is shown a section elevation of device 1 as taken through FIG. 1.

The flash back chamber 2 is shown as being circumferential in configuration, however it could be square, rectangular or any other configuration by design choice.

The needle release button 9 is shown with a first end and a second end. The depressor knob 18 is shown on the first end and the stop knob 19 is shown near the second end. An anti rotation guide 27 is shown at the second end of the needle release button 9. The anti rotation guide 27 is shown disposed in the anti rotation slot 28 formed in the inclined plane latch 8. The biased spring hard needle 3 with a cannula is shown suitably fixed to the inclined plane latch 8. The anti rotation guide 27 that is suitably disposed in the anti rotation slot 28 will prevent the inclined plane latch 8 from rotating 29 during use.

Figure 3:
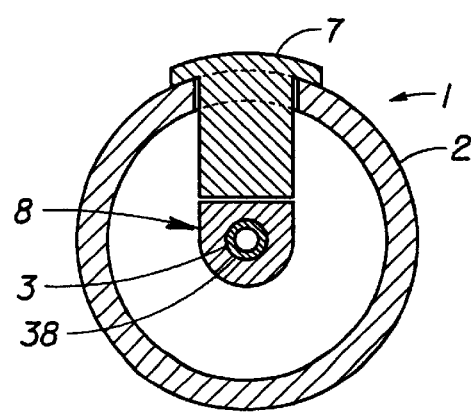
FIG. 3 is a section elevation view of the device as taken through FIG. 1.

Referring to FIG. 3 there is shown a section elevation of the device 1 as taken through FIG. 1.

The flash back chamber 2 is shown supporting the latch foundation 7. The biased spring hard needle 3 with a cannula 38 is shown fixed to the inclined plane latch 8.

Figure 4:
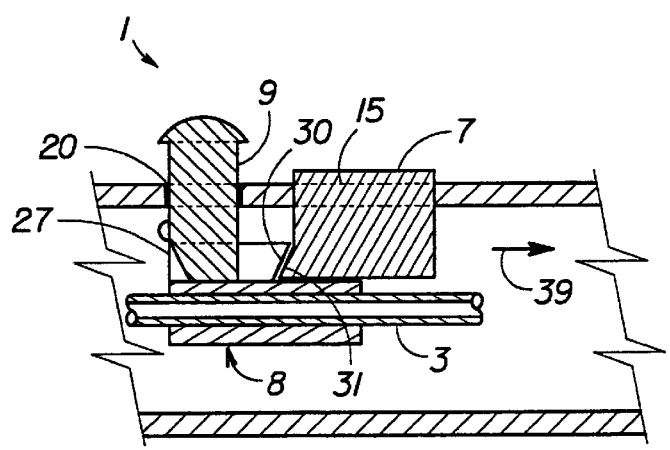
FIG. 4 is a section elevation view of the device as taken through FIG. 2.

Referring to FIG. 4 there is shown a section elevation of the device 1 as taken through FIG. 2.

The needle release button 9 is shown disposed in the needle release hole 20. The latch foundation 7 is shown fixed to the flash back chamber 2 at the first hole 15. The anti rotation guide 27 is shown suitably disposed in the anti rotation slot formed in the needle release button 9. The biased spring hard needle 3 is shown suitably fixed to the inclined plane latch 8.

The latch inclined plane 30 is shown pressed against and hooked to the foundation inclined plane 31. The biased spring hard needle 3 is pulling the inclined plane latch 8 and the latch incline plane 30 hard against the foundation inclined plane 31 of the latch foundation 7 thereby preventing the inclined plane latch 8 and the first end of the biased spring hard needle 3 from moving in a retract direction 39. Only the second end of the biased spring hard needle 3 is biased into a spring; the first end of the biased spring hard needle is a straight hard needle.

Figure 5:
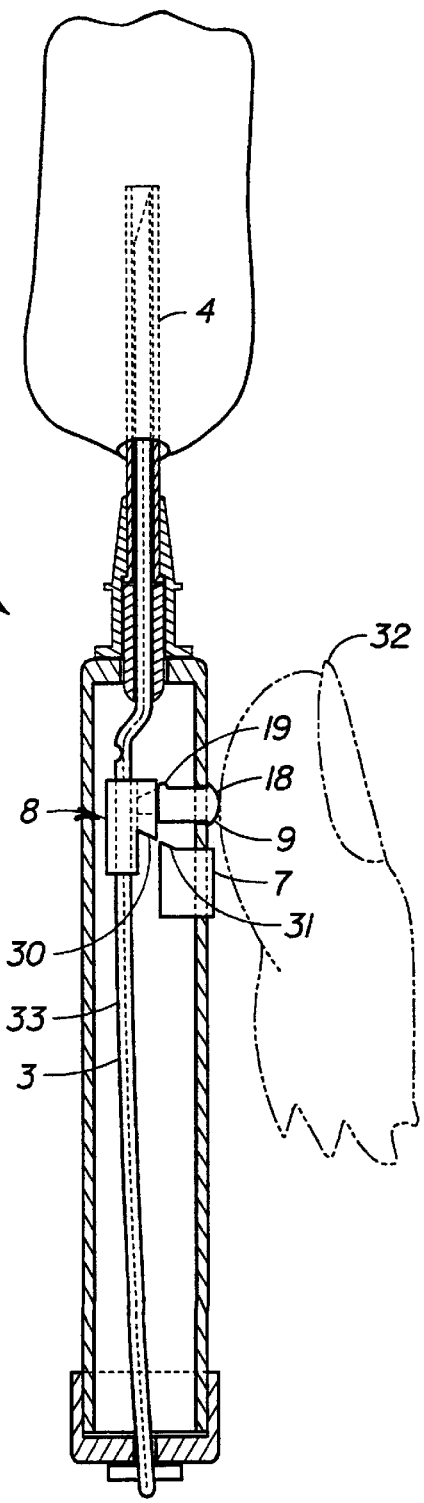

Referring to FIG. 5 there is shown a section elevation of the device 1 as it is about to be retracted.

A finger 32 or thumb is shown depressing the needle release button 9 therein thrusting the inclined plane latch 8 away from the latch foundation 7 and disengaging the latch incline plane 30 from the foundation incline plane 31. The biased spring hard needle 3 acts as a transverse spring and therefore resists the thrust from the finger 32 and the needle release button 9, however, the biased spring hard needle 3 deflects 33 some or bends some thereby releasing the hook like grasp that the latch inclined plane 30 had on the foundation inclined plane 31. The position shown in FIG. 5 should last only a brief moment as the biased second end of the first end on the biased spring hard needle 3 is pulled out from the soft catheter 4.

Figure 6:
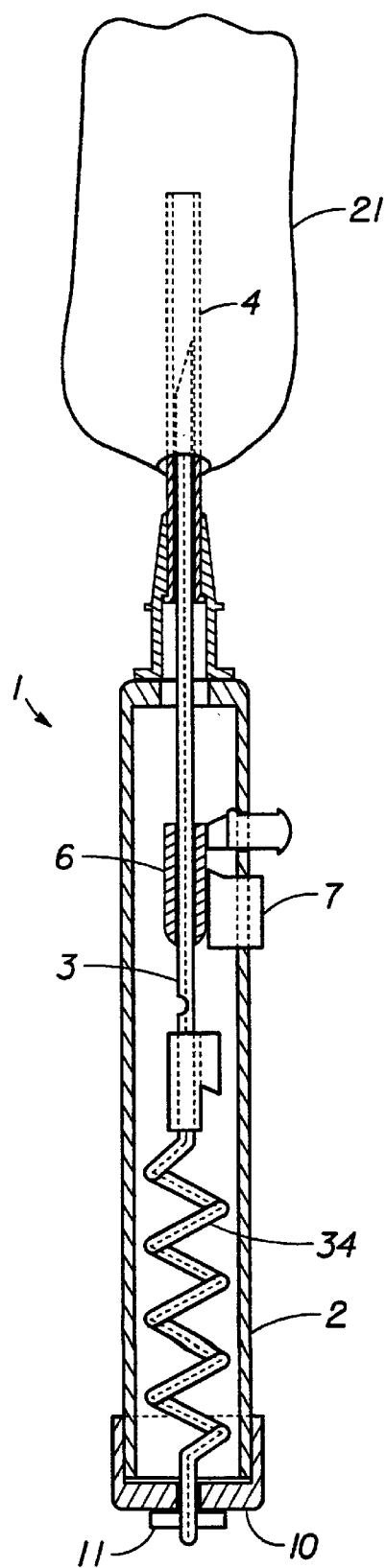
FIG. 6 is a section elevation view of the device showing the device being disabled.

Referring to FIG. 6 there is shown a continuation of the retraction of the biased spring hard needle 3 of the device 1.

The second end of the biased spring hard needle 3 is forming into a coil 34. The first end of the biased spring hard needle 3 is being withdrawn from the soft catheter 4 leaving the soft catheter 4 in the body 21. The second end of the hub post 6 is shown as tapered to prevent it from catching a corner of the latch foundation 7. Only the second end of the biased spring hard needle 3 is fixed to the second end of the flash back chamber 2 by way of the end cap 10 and end bar 11.

Figure 7:
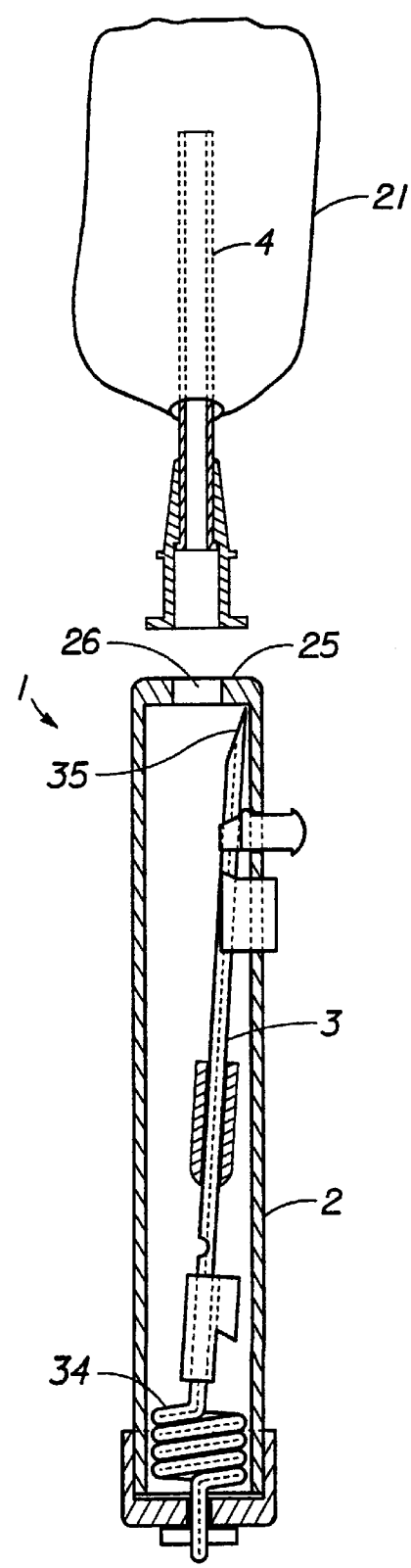
FIG. 7 is a section elevation view of the device disabled.

Referring to FIG. 7 there is shown a section elevation of the device 1 with the biased spring hard needle 3 retracted.

The biased spring hard needle 3 is no longer biased; the second end has formed into a coil 34 and is permanently pulling or holding the first end of the biased spring hard needle 3 inside of the flash back chamber 2. The coil 34 is also causing the biased spring hard needle 3 to rest at an angle within the flash back chamber 2 thereby preventing the point 35 at the first end of the biased spring hard needle 3 from re-entering the flange hole 26 formed in the flash back chamber flange 25.

The soft catheter 4 is shown left in the body 21 where it will be suitably attached or fixed to other devices.

Figure 8:
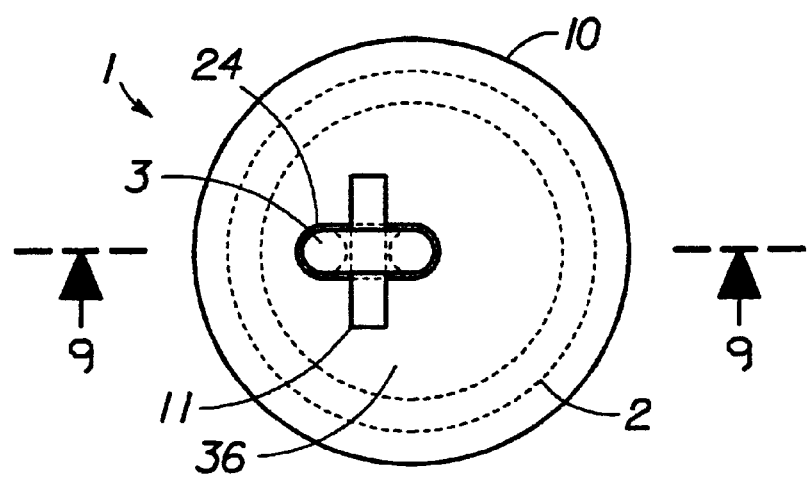
FIG. 8 is an end view of the end cap.

Referring to FIG. 8 there is shown a view of the end cap 10 of the device 1.

The cap hole 24 is formed at the second end of the end cap 10 and extends from the first side to the second side of the end cap cover 36. The second end of the biased spring hard needle 3 is formed into a loop or hook and extends through the end cap cover 36 wherein an end bar 11 is inserted into the loop or hook to capture and hold the biased spring hard needle 3. The end bar 11 is suitably fixed to the end cap cover 36 by adhesive, welding, rivets or other suitable means by design choice.

Figure 9:
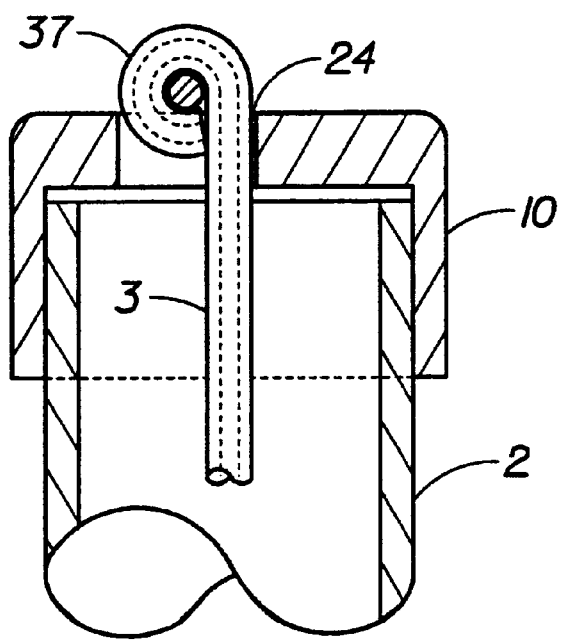
FIG. 9 is a section view as taken through FIG. 8.

Referring to FIG. 9 there is shown a section elevation of the end cap 10 as taken through FIG. 8.

The second end of the biased spring hard needle 3 is formed into a loop 37 wherein the entire loop 37 is disposed or could be disposed in the cap hole 24. The end cap 10 is suitably fixed to the second end of the flash back chamber 2 by adhesive, threads, rivets, or welding or other suitable means by design choice.

Although the system described in detail supra has been found to be most satisfactory and preferred, many variations are possible. For example the second end of the soft catheter may be provided with valves to suitably stop the flow of blood while other devices are being attached or removed from the soft catheter, or the latch means could be placed in another location.

Although the invention has been described with reference to the preferred embodiment, it will be understood by those skilled in the art, that additions, modifications, substitutions, deletions and other changes not specifically described, may be made in the embodiment herein, it should be understood that the details herein are to be interpreted as illustrative and are not in a limiting sense.

What is claimed as invention is:

1. A device for latching and releasing a biased needle comprising:
    an elongated chamber having a first end and a second end;
    a biased spring needle with a first end extending past said first end of said flash back chamber and a second end fixed near said second end of said flash back chamber;
    an inclined plane latch with a first end, a second end and a third end, wherein a first latch inclined plane is formed on said third ends and wherein said incline plane latch is fixed to said biased spring needle;
    a latch foundation with a first end, a second end and a third end, wherein said latch foundation is fixed to said flash back chamber at said third end of said latch foundation, wherein a second latch inclined plane is formed at said first end of said latch foundation and wherein said second latch inclined plane is engaged with said first latch incline plane;
    an anti rotation slot formed in said third end of said inclined plane latch;
    a needle release button with a first end and a second end, wherein an anti rotation guide is formed in said second end of said needle release button and is disposed into said anti rotation slot formed in said inclined plane latch to prevent said inclined plane latch from rotating when said needle release button is depressed causing said latch inclined plane to be pushed away from and disengaged with said foundation inclined plane thus releasing said inclined plane latch from said latch foundation thereby allowing said biased spring hard needle to be withdrawn completely into said flash back chamber.

2. The device of claim 1, wherein said device may be used on a blood sampling device.

3. The device of claim 1, wherein said device may be used on a syringe.

4. A device for latching and releasing a biased needle comprising:
    a chamber having a first end, a second end, and a latch foundation formed within the chamber;
    a biased needle extending within the chamber and having a latch engaging the latch foundation;
    a needle release button extending into the chamber in alignment with the latch for disengaging the latch from the latch foundation.

5. The device of claim 4, wherein the latch and the latch foundation form inclined planes.

6. The device of claim 4, wherein needle release button is disposed to prevent rotation of the latch.

7. The device of claim 4, wherein the biased needle is a spring needle.

8. The device of claim 4, wherein the chamber is part of a blood sampling device.

9. The device of claim 4, wherein the chamber is part of a syringe.

10. A device for latching and releasing a biased needle comprising:

an elongated flash back chamber having a first end, a second end, a latch foundation formed within the chamber;

a biased needle extending between the first and second ends of the chamber and having a latch engaging the latch foundation, wherein the biased needle biases the latch against the latch foundation;

a needle release button extending into the chamber in alignment with the latch for thrusting the latch away from the latch foundation.

11. The device of claim 10, wherein the latch and the latch foundation form inclined planes.

12. The device of claim 11, wherein the biased needle is a spring needle.

13. The device of claim 11, wherein the chamber is part of a blood sampling device.

14. The device of claim 11, wherein the chamber is part of an IV catheter.

* * * * *